US008642791B2

(12) United States Patent (10) Patent No.: US 8,642,791 B2
Dumesic et al. (45) Date of Patent: Feb. 4, 2014

(54) LEWIS AND BRONSTED-LOWRY ACID-CATALYZED PRODUCTION 5-HYDROXYMETHYLFURFURAL (HMF) FROM GLUCOSE

(75) Inventors: James A. Dumesic, Verona, WI (US); Yomaira J. Pagán-Torres, Madison, WI (US); Tianfu Wang, Ames, IA (US); Brent Howard Shanks, Ames, IA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 104 days.

(21) Appl. No.: 13/313,389

(22) Filed: Dec. 7, 2011

(65) Prior Publication Data

US 2013/0150595 A1 Jun. 13, 2013

(51) Int. Cl.
*C07D 307/46* (2006.01)
(52) U.S. Cl.
USPC ......................................................... 549/488
(58) Field of Classification Search
USPC ......................................................... 549/488
See application file for complete search history.

(56) References Cited

U.S. PATENT DOCUMENTS

| | | | |
|---|---|---|---|
| 3,071,599 A | 1/1963 | Hales et al. | |
| 3,483,228 A | 12/1969 | Garber et al. | |

FOREIGN PATENT DOCUMENTS

CN 101381351 A 3/2009

OTHER PUBLICATIONS

Hansen, Thomas S., et al., "Synergy of boric acid and added salts in the catalytic dehydration of hexoses to 5-hydroxymethylfurfural in water," Green Chemistry, vol. 13, No. 1, Nov. 30, 2010, pp. 109-114.
Pagan-Torres, Yomaira J., et al., "Production of 5-Hydroxymethylfurfural from Glucose Using a Combination of Lewis and Bronsted Acid Catalysts in Water in a Biphasic Reactor with an Alkylphenol Solvent," ACS Catalysis, vol. 2, No. 6, Apr. 18, 2012, pp. 930-934.
Wang, Tianfu, et al., "Water-Compatible Lewis Acid-Catalyzed Conversion of Carbohydrates to 5-Hydroxymethylfurfural in a Biphasic Solvent System," Topics in Catalysis, vol. 55, No. 7-10, Jun. 19, 2012, pp. 657-662.
Wang, Jianjian, et al., "Direct conversion of carbohydrates to 5-hydroxymethylfurfural using Sn-Mont catalyst," Green Chemistry, vol. 14, No. 9, Jul. 4, 2012, pp. 2506-2512.
De et al., 2011, Microwave assisted conversion of carbohydrates and biopolymers to 5-hydroxymethylfurfural with aluminum chloride catalyst in water, Green Chem., 13, 2859-2868.
Alonso et al., Production of Biofuels from Cellulose and Corn Stover Using Alkylphenol Solvents, ChemSusChem 2011, 4, 1078-1081.
Baes et al., The Hydrolysis of Cations; Wiley: New York, 1976.
Binder et al., Simple Chemical Transformation of Lignocellulosic Biomass into Furans for Fuels and Chemicals, J. Am. Chem. Soc. 2009, 131, 1979-1985.
Buntara et al., Caprolactam from Renewable Resources: Catalytic Conversion of 5-Hydroxymethylfurfural into Caprolactone, Angew. Chem. Int. Ed. 2011, 50, 7083-7087.
Chidambaram et al., A two-step approach for the catalytic conversion of glucose to 2,5-dimethylfuran I ionic liquids, Green Chem. 2010, 12, 1253-1262.
Corma et al., Chemical routes for the Transformation of Biomass Into Chemicals, Chem. Rev. 2007, 107, 2411-2502.
Fringuelli et al., $AlCl_3$ as an efficient Lewis acid catalyst in water, Tetrahedron Lett. 2001, 42, 1131-1133.
Fringuelli et al., Lewis-Acid Catalyzed Organic Reactions in Water. The Case of $AlCl_3$, $TiCl_4$, and $SnCl_4$ Believed to be Unusable in Aqueous Medium, J. Org. Chem. 2001, 66, 4719-4722.
Gandini et al., Furans in Polymer Chemistry, Prog. Polymer Science 1997, 22, 1203-1379.
Hu et al., Efficient conversion of glucose into 5-hydroxymethylfurfural catalyzed by a common lewis acid $SnCl_4$ in an ionic liquid, Green Chem 2009, 11, 1746-1749.
Huang et al., Integrating enzymatic and acid catalysts to convert glucose into 5-hydroxymethylfurfural, Chem. Comm. 2010, 46, 1115-1117.
Ishida et al., Catalytic activity of lanthanoide(III) ions for dehydration of D-glucose to 5-(hydroxymethyl)furfural, J. Mol. Catal. A: Chem. 1996, 112, 163-165.
Jackson et al., Chemical and thermodynamic constraints on the hydrothermal transport and deposition of tin: I. Calculation of the solubility of cassiterite at high pressures and temperatures, Geochim. Cosmochim. Ac. 1985, 49, 1-22.
Lewkowski, J., Synthesis, chemistry and applications of 5-hydroxymethylfurfural and its derivatives, Arkivoc 2001, 17-54.
Moreau et al., Recent catalytic advances in the chemistry of substituted furans from carbohydrates and in the ensuing polymers, Top. Catal. 2004, 27, 11-29.
Moreau et al., Dehydration of fructose and sucrose into 5-hydroxymethylfurfural in the presence of 1-H-3-methyl imidazolium chloride acting both as a solvent and catalyst, J. Mol. Catal. A: Chem. 2006, 253, 165.
Nagorski et al., Mechanistic Imperatives for Aldose-Ketose Isomerization in Water: Specific, General Base- and Metal Ion-Catalyzed Isomerization of Glycerldehyde with Proton and Hydride Transfer, J. Am. Chem. Soc. 2001, 123, 794-802.
Nikolla et al., "One-Pot" Synthesis of 5-(hydroxymethyl(furfural) from Carbohydrates using Tin-beta Zeolite, ACS Catal. 2011, 1, 408-410.
Pidko et al., Glucose Activation by Transient $Cr^{2+}$ Dimers, Angew. Chem. Int. Ed. 2010, 49, 2530-2534.

(Continued)

*Primary Examiner* — Bernard Dentz
(74) *Attorney, Agent, or Firm* — Joseph T. Leone, Esq.; DeWitt Ross & Stevens S.C.

(57) ABSTRACT

Described is a process to make hydroxymethylfurfural (HMF) from glucose. The process includes the steps of reacting a feedstock solution comprising glucose, in the presence of a homogeneous Brønsted acid catalyst and a homogeneous Lewis acid catalyst, in a reaction vessel containing a biphasic reaction medium. The reaction medium includes an aqueous reaction solution and a substantially immiscible organic extraction solution. HMF is produced in the aqueous reaction solution and extracted into the organic extraction solution.

14 Claims, 5 Drawing Sheets

(56) References Cited

OTHER PUBLICATIONS

Robyt, J. F., Transformations, *Essentials of Carbohydrate Chemistry*; Springer: New York 1998; p. 48-74.

Román-Leshkov et al., Phase Modifiers Promote Efficient Production of Hydroxymethylfurfural from Fructose, *Science* 2006, 312, 1933-1937.

Román-Leshkov et al., Solvent Effects on Fructose Dehydration to 5-Hydroxymethylfurfural in Biphasic Systems Saturated with Inorganic Salts, *Top. Catal.* 2009, 52, 297-303.

Román-Leshkov et al., Mechanism of glucose Isomerization Using a Solid Lewis Acid Catalyst in Water, *Angew. Chem. Int. Ed.* 2010, 49, 8954-8957.

Seri et al., Catalytic Activity of Lanthanide(III) Ions for the Dehydration of Hexose to 5-Hydroxymethy1-2-furaldehyde in Water, *Bull. Chem. Soc. Jpn.* 2001, 74, 1145-1150.

Stahlberg et al., Metal-Free Dehydration of Glucose to 5-(Hydroxymethyl)furfural in Ionic Liquids with Boric Acid as a Promoter, *Chem-Eur. J.* 2011, 17, 1456-1464.

Takagaki et al., A one-pot reaction for biorefinery: combination of solid acid and base catalysts for direct production of 5-hydroxymethylfurfural from saccharides, *Chem. Comm.* 2009, 6276-6278.

Yang et al., Alkaline degradation of glucose: effect of initial concentration of reactants, *Carbohyd. Res.* 1996, 280, 27-45.

Zakrzewska et al., Ionic Liquid mediated Formation of 5-Hydroxymethylfurfural—A Promising Biomass-Derived Building Block, *Chem. Rev.* 2010, 111, 397-417.

Zhao et al., *Science* 2007, 316, 1597-1600.

//# LEWIS AND BRØNSTED-LOWRY ACID-CATALYZED PRODUCTION 5-HYDROXYMETHYLFURFURAL (HMF) FROM GLUCOSE

FEDERALLY FUNDED RESEARCH STATEMENT

This invention was made with government support under 0520527 and 0813570 awarded by the National Science Foundation. The government has certain rights in this invention.

FIELD OF THE INVENTION

Disclosed and claimed herein is a method to produce hydroxymethylfurfural (HMF) from glucose via a two-phase reaction utilizing both Lewis acid catalysts and Brønsted-Lowry acid catalysts.

BACKGROUND

Biomass has been intensely investigated as a renewable feedstock for the production of chemicals and transportation fuels in view of economic, environmental, and political concerns associated with diminishing fossil fuel resources. The development of economically viable processes for the production of chemical intermediates from biomass-derived carbohydrates has become an important challenge for research in this area, such as the development of efficient processes for the production of the platform chemical 5-hydroxymethylfurfural (HMF).[1] In this respect, HMF has been identified as a primary building block for the production of furanic polyesters, polyamides, and polyurethanes analogous to those derived from the petroleum polymer industry.[2]

Conventionally, HMF is produced from the acid-catalyzed dehydration of $C_6$-sugars (i.e., hexoses). The formation of HMF is proposed to take place through the dehydration of a 5-member monosaccharide ring. Hence, fructose, which contains 21.5% of furanose tautomers in aqueous solution, can be converted to HMF more efficiently than glucose which contains 1% of furanose tautomers in aqueous solutions.[3] Accordingly, while considerable efforts have focused on the production of HMF from fructose in high yields,[1a, 1c, 1d] there remains a long-felt and unmet need for a catalytic system that efficiently converts glucose to HMF in water.

While the dehydration of fructose is catalyzed by strong acids, the challenge for the conversion of glucose to HMF is to find a catalytic system that can selectively isomerize glucose to fructose in tandem with the dehydration reaction. Glucose isomerization proceeds by hydrogen transfer from the C-2 to the C-1 position and from the O-2 to the O-1 position of the α-hydroxy aldehyde to form the α-hydroxy ketone.[4] The mechanism of hydrogen transfer from the O-2 to the O-1 position of the aldose is by a proton transfer between the electronegative carbonyl and hydroxyl groups, whereas the transfer of hydrogen from the C-2 to the C-1 position may occur through a hydride ion, or in alkaline conditions as a proton.[5] Lewis acids and Brønsted bases are catalysts commonly used for this reaction. However, basic catalysts typically lead to side reactions.[6]

Recent studies have been published on developing new processing strategies focused on isomerizing glucose to fructose with a subsequent acid-catalyzed dehydration of fructose to HMF. Lewis acid catalysts in ionic liquids have been shown to be the most promising systems for the conversion of glucose to HMF.[1e] Zhao, et al. first reported HMF yields of 68-70% in a system consisting of 1-ethyl-3-methyl-imidazolium chloride and a $CrCl_2$ catalyst.[1b] It is believed that the high activity and selectivity observed for the production of HMF in ionic liquids with chromium catalysts are caused by the stabilization of the transition state for ring opening of glucose by the Lewis acidic Cr center during glucose isomerization.[7] Other studies have been carried out on this same reaction using different ionic liquids or Lewis acid catalysts.[8] However, the reactions require ionic liquids, which are expensive and subject to deactivation by small amounts of water formed during dehydration reactions.[9] Binder, et al. reported that a mixture consisting of dimethylacetamide (DMA), NaBr, and a Lewis acid, $CrCl_2$, could reach HMF yields of 81%, being as effective as ionic liquid systems.[1c] Huang, et al. reported an HMF yield of 63% from glucose by a two-step process consisting of the isomerization of glucose to fructose in the presence of glucose isomerase and borate ions, followed by the acid catalyzed dehydration of fructose to HMF using HCl as a catalyst in a biphasic system.[10] Takagaki, et al. reported HMF yields of 42% at a 73% conversion by a similar two step process by combining a solid acid catalyst, Amberlyst-15, and a solid base catalyst, Mg—Al hydrotalcite, in N,N-dimethylformamide.[11] Nikolla, et al. reported HMF yields of 57% at 79% conversion of glucose using a Lewis acidic Sn-Beta zeolite and HCl in a water/NaCl/THF biphasic reaction system.[12]

SUMMARY OF THE INVENTION

While glucose can be converted with low yields to HMF using Brønsted acids, the method disclosed herein greatly increases the yield from glucose to HMF by first isomerizing the glucose to fructose, and dehydrating the fructose to HMF. The method takes place in an aqueous solution, rather than in an ionic liquid. Preferably the two reactions (isomerization and dehydrogenation) are conducted simultaneously in a biphasic reaction system in which the HMF spontaneously separates into a non-aqueous phase. This greatly increases the efficiency of separating the desired HMF product from the reactants. The reaction is preferably carried out continuously, but can also be run in batch fashion.

Disclosed is a process to make hydroxymethylfurfural (HMF) from glucose, glucose-containing oligomers, glucose-containing polymers, or combinations thereof. A first version of the process comprises reacting a feedstock solution comprising glucose, glucose-containing oligomers, glucose-containing polymers, or combinations thereof, in the presence of a homogeneous Brønsted acid catalyst and a homogeneous Lewis acid catalyst, in an aqueous reaction solution, to yield a product solution comprising HMF. The process may further comprise extracting the HMF into a substantially immiscible organic extraction solution. It is generally, preferred, although not required, that the reacting step and the extracting step take place simultaneously in a reaction vessel containing a biphasic reaction medium comprising an aqueous reaction solution and a substantially immiscible organic extraction solution, and wherein HMF formed in the aqueous reaction solution is extracted into the organic extraction solution. The process may also take place in a mono-phasic system comprising only the aqueous reaction phase. It is preferred that the process use homogeneous catalysts. If a biphasic system is used, heterogeneous acid catalysts may also be used.

The substantially immiscible organic extraction solution preferably comprises at least one alkylphenol. The alkylphenol (AP) may be selected from those having the structure:

wherein $R^1$-$R^5$ are independently selected from the group consisting of hydrogen, hydroxyl, esters, ethers, carboxylic acids, and $C_1$-$C_{24}$ linear, branched, or cyclic alkyl or alkene, provided that at least one of $R^1$-$R^5$ is an alkyl group. In certain versions of the process, it is preferred that the AP has at least one and no more than two of $R^1$-$R^5$ as a $C_1$-$C_{12}$ or $C_1$-$C_6$ linear, branched, or cyclic alkyl group.

The Lewis acid catalyst is preferably selected from the group consisting of Lewis acids comprising a lathanoid metal, a metal from any of Groups 4, 5, 13, 14 and 15 of the periodic table of the elements, and combinations thereof. This is preferred only, and many other Lewis acids will function in the process. (See the definition of Lewis acid, below.) Preferably, the Brønsted acid catalyst is selected from the group consisting of mineral acids, organic acids, heteropolyacids, solid acid catalysts, zeolites, and combinations thereof. Again, this is preferred only. Many other Brønsted acids will function in the process. (See the definition of Brønsted acid, below.)

In certain versions of the process, the aqueous reaction solution has an amount of NaCl dissolved therein, or the aqueous reaction solution is saturated with NaCl. A saturated aqueous solution of NaCl is approximately 6 M NaCl. Thus, the aqueous reaction solution may optionally contain from 0 M NaCl to about 6 M NaCl, or any range between 0 M and about 6M (e.g., a lower NaCl concentration of 0 M, 1 M, 2 M, 3 M, 4 M, or 5 M; and an upper NaCl concentration of 6 M, 5 M, 4 M, 3 M, 2 M, or 1 M).

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and devices described herein can comprise, consist of, or consist essentially of the essential elements and limitations of the methods and devices described herein, as well as any additional or optional ingredients, components, or limitations described herein or otherwise useful in synthetic organic chemistry or chemical engineering.

BRIEF DESCRIPTION OF THE DRAWINGS

FIGS. 1A-1F: Glucose conversion in a biphasic system with HCl and various Lewis Acids as a function of time. FIG. 1A: $AlCl_3$; FIG. 1B: $SnCl_4$; FIG. 1C $VCl_3$; FIG. 1D: $GaCl_3$: FIG. 1E: $InCl_3$; and FIG. 1F: no Lewis acid. In each figure: (■)=glucose, (○)=fructose, and (▲)=HMF.

DETAILED DESCRIPTION

Abbreviations and Definitions

The following abbreviations and definitions are used throughout the specification and claims. Terms not given a specific definition are to be accorded their accepted definition in the fields of chemistry and/or chemical engineering.

AP=alkylphenol. As used herein, an alkylphenol is defined as a compound having the formula:

wherein $R^1$-$R^5$ are independently selected from the group consisting of hydrogen, hydroxyl, esters, ethers, carboxylic acids, and $C_1$-$C_{24}$ linear, branched, or cyclic alkyl or alkene, provided that at least one of $R^1$-$R^5$ is alkyl. All positional isomers (ortho, meta, para) are explicitly included, as are compounds having more than one hydroxy group, e.g., alkyl-substituted-1,4-dihydroxybenzene. Mono- and di-alkylphenols are preferred, as are APs wherein the alkyl substituent(s) is a $C_1$-$C_{12}$ linear, branched, or cyclic alkyl, more preferably still a $C_1$ to $C_6$ linear or branched alkyl.

"Biomass" as used herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. "Biomass" includes virgin biomass and/or non-virgin biomass such as agricultural biomass, commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like.

"Biomass-derived"=Compounds or compositions fabricated or purified from biomass. Glucose for use in the disclosed method may be biomass-derived.

Brønsted-Lowry Acid/Base=A Brønsted-Lowry acid is defined herein as any chemical species (atom, ion, molecule, compound, complex, etc.), without limitation, that can donate or transfer one or more protons to another chemical species. Mono-protic, diprotic, and triprotic acids are explicitly included within the definition. A Brønsted-Lowry base is defined herein as any chemical species that can accept a proton from another chemical species. Included among Brønsted-Lowry acids are mineral acids, organic acids, heteropolyacids, solid acid catalysts, zeolites, etc. as defined herein. Note that this list is exemplary, not exclusive. The shortened term "Brønsted" is also used synonymously with "Brønsted-Lowry."

"Glucose-containing oligomers, glucose-containing polymers"=Any chemical species, having any type of intramolecular bond type, that comprises a glucose unit. The definition explicitly includes glucose-containing disaccharides (such as, but not limited to, sucrose, lactose, maltose, trehalose, cellobiose, kojibiose, nigerose, isomaltose, β,β-trehalose, α,β-trehalose, sophorose, laminaribiose, gentiobiose, turanose, maltulose, palatinose, gentiobiulose, etc.), trisaccharides (such as, but not limited to, isomaltotriose, nigerotriose, maltotriose, maltotriulose, raffinose, etc.), and larger oligosaccharides and polysaccharides, as well as large and more complex glucose-containing polymers and carbohydrates, such as, but not limited to, starch, amylase, amylopectin, glycogen, cellulose, hemicelluloses (e.g., xyloglucan, glucomannan, etc.), lignocellulose, and the like. Linear, branched, and macrocyclic oligomers and polymers containing glucose are explicitly included within the definition.

"Heteropolyacid"=A class of solid-phase acids exemplified by such species as $H_4SiW_{12}O_{40}$, $H_3PW_{12}O_{40}$, $H_6P_2W_{18}O_{62}$, $H_{3+x}PMo_{12-x}V_xO_{40}$ and the like. Heteropolyacids are solid-phase acids having a well-defined local structure, the most common of which is the tungsten-based Keggin structure. The Keggin unit comprises a central $PO_4$ tetrahedron, surrounded by 12 $WO_6$ octahedra. The standard unit has a net (⁻3) charge, and thus requires three cations to satisfy electroneutrality. If the cations are protons, the material functions as a Brønsted acid. The acidity of these compounds (as well as other physical characteristics) can be "tuned" by substituting different metals in place of tungsten in the Keggin structure. See, for example, Bardin et al. (1998) "Acidity of Keggin-Type Heteropolycompounds Evaluated by Catalytic Probe Reactions, Sorption Microcalorimetry and Density Functional Quantum Chemical Calculations," *J. of Physical Chemistry B*, 102:10817-10825.

"HMF"=Hydroxymethylfurfural.

"Homogeneous catalyst"=A catalyst that exists in the same phase (solid, liquid, or gas) as the reactants.

"Lewis Acid/Base"=A Lewis acid is defined herein as any chemical species that is an electron-pair acceptor, i.e., any chemical species that is capable of receiving an electron pair, without limitation. A Lewis base is defined herein as any chemical species that is an electron-pair donor, that is, any chemical species that is capable of donating an electron pair, without limitation.

In preferred versions of the invention, the Lewis acid (also referred to as the Lewis acid catalyst) may be any Lewis acid based on transition metals, lathanoid metals, and metals from Group 4, 5, 13, 14 and 15 of the periodic table of the elements, including boron, aluminum, gallium, indium, titanium, zirconium, tin, vanadium, arsenic, antimony, bismuth, lanthanum, dysprosium, and ytterbium. One skilled in the art will recognize that some elements are better suited in the practice of the method. Illustrative examples include $AlCl_3$, $(alkyl)AlCl_2$, $(C_2H_5)_2AlCl$, $(C_2H_5)_3Al_2Cl_3$, $BF_3$, $SnCl_4$ and $TiCl_4$.

The Group 4, 5 and 14 Lewis acids generally are designated by the formula $MX_4$; wherein M is Group 4, 5, or 14 metal, and X is a halogen independently selected from the group consisting of fluorine, chlorine, bromine, and iodine, preferably chlorine. X may also be a psuedohalogen. Non-limiting examples include titanium tetrachloride, titanium tetrabromide, vanadium tetrachloride, tin tetrachloride and zirconium tetrachloride. The Group 4, 5, or 14 Lewis acids may also contain more than one type of halogen. Non-limiting examples include titanium bromide trichloride, titanium dibromide dichloride, vanadium bromide trichloride, and tin chloride trifluoride.

Group 4, 5 and 14 Lewis acids useful in the method may also have the general formula $MR_nX_{4-n}$; wherein M is Group 4, 5, or 14 metal; wherein R is a monovalent hydrocarbon radical selected from the group consisting of $C_1$ to $C_{12}$ alkyl, aryl, arylalkyl, alkylaryl and cycloalkyl radicals; wherein n is an integer from 0 to 4; and wherein X is a halogen independently selected from the group consisting of fluorine, chlorine, bromine, and iodine, preferably chlorine. X may also be a psuedohalogen. Non-limiting examples include benzyltitanium trichloride, dibenzyltitanium dichloride, benzylzirconium trichloride, dibenzylzirconium dibromide, methyltitanium trichloride, dimethyltitanium difluoride, dimethyltin dichloride and phenylvanadium trichloride.

Group 4, 5 and 14 Lewis acids useful in method may also have the general formula $M(RO)_nR'_mX_{(m+n)}$; wherein M is Group 4, 5, or 14 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is an integer from 0 to 4; m is an integer from 0 to 4 such that the sum of n and m is not more than 4; and X is a halogen independently selected from the group consisting of fluorine, chlorine, bromine, and iodine, preferably chlorine. X may also be a psuedohalogen. Non-limiting examples include methoxytitanium trichloride, n-butoxytitanium trichloride, di(isopropoxy)titanium dichloride, phenoxytitanium tribromide, phenylmethoxyzirconium trifluoride, methyl methoxytitanium dichloride, methyl methoxytin dichloride and benzyl isopropoxyvanadium dichloride.

Group 5 Lewis acids may also have the general formula $MOX_3$; wherein M is a Group 5 metal; X is a halogen independently selected from the group consisting of fluorine, chlorine, bromine, and iodine, preferably chlorine. A non-limiting example is vanadium oxytrichloride.

The Group 13 Lewis acids have the general formula $MX_3$; wherein M is a Group 13 metal and X is a halogen independently selected from the group consisting of fluorine, chlorine, bromine, and iodine, preferably chlorine. X may also be a psuedohalogen. Non-limiting examples include aluminum trichloride, boron trifluoride, gallium trichloride, indium trifluoride, and the like.

The Group 13 Lewis acids useful in method may also have the general formula: $MR_nX_{3-n}$ wherein M is a Group 13 metal; R is a monovalent hydrocarbon radical selected from the group consisting of $C_1$ to $C_{12}$alkyl, aryl, arylalkyl, alkylaryl and cycloalkyl radicals; and n is an number from 0 to 3; and X is a halogen independently selected from the group consisting of fluorine, chlorine, bromine, and iodine, preferably chlorine. X may also be a psuedohalogen. Non-limiting examples include ethylaluminum dichloride, methylaluminum dichloride, benzylaluminum dichloride, isobutylgallium dichloride, diethylaluminum chloride, dimethylaluminum chloride, ethylaluminum sesquichloride, methylaluminum sesquichloride, trimethylaluminum and triethylaluminum.

Group 13 Lewis acids useful in this disclosure may also have the general formula $M(RO)_nR'_mX_{3-(m+n)}$; wherein M is a Group 13 metal; RO, is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$alkyl, aryl, arylalkyl, alkylaryl and cycloalkyl radicals; n is a number from 0 to 3; m is an number from 0 to 3 such that the sum of n and in is not more than 3; and X is a halogen independently selected from the group consisting of fluorine, chlorine, bromine, and iodine, preferably chlorine. X may also be a psuedohalogen. Non-limiting examples include methoxyaluminum dichloride, ethoxyaluminum dichloride, 2,6-di-tert-butylphenoxyaluminum dichloride, methoxy methylaluminum chloride, 2,6-di-tert-butylphenoxy methylaluminum chloride, isopropoxygallium dichloride and phenoxy methylindium fluoride.

Group 13 Lewis acids useful in this disclosure may also have the general formula $M(RC(O)O)_nR'_mX_{3-(m+n)}$; wherein M is a Group 13 metal; RC(O)O is a monovalent hydrocarbacyl radical selected from the group consisting of $C_2$ to $C_{30}$ alkacyloxy, arylacyloxy, arylalkylacyloxy, alkylarylacyloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3 and m is a number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include acetoxyaluminum dichloride, benzoyloxyaluminum dibromide, benzoyloxygallium difluoride, methyl acetoxyaluminum chloride, and isopropoyloxyindium trichloride.

The most preferred Lewis acids for use in the method are metal halides generally and more specifically transition metal halides, lathanoid metal halides, and Group 5, 13, and 14 metal halides. Preferred among the metal halides are metal chlorides. Preferred transition metal chlorides include, but are not limited to, $TiCl_4$, $VCl_3$.and the like. Preferred Group 13 and 14 metal halides and chlorides include, but are not limited to, $BF_3$, $AlCl_3$, $SnCl_4$, $InCl_3$, and $GaCl_3$. Preferred lanthanoid chlorides include, but are not limited to, $LaCl_3$, $DyCl_3$ and $YbCl_3$.

Mineral acid=any mineral-containing acid, including (by way of example and not limitation), hydrochloric acid, nitric acid, phosphoric acid, sulfuric acid, boric acid, hydrofluoric acid, hydrobromic acid, hydroiodic acid, and the like.

Organic acid=any organic acid, without limitation, such as toluensulfonic acid, formic acid, acetic acid, oxalic acid, trifluoroacetic acid, and the like.

SBP=sec-butyl phenol.

A "solid acid catalyst" can comprise one or more solid acid materials. The solid acid catalyst can be used independently or alternatively can be utilized in combination with one or more mineral acid or other types of catalysts. Exemplary solid acid catalysts include, but are not limited to, heteropoly acids, acid resin-type catalysts, meso-porous silicas, acid clays, sulfated zirconia, molecular sieve materials, zeolites, and acidic material on a thermo-stable support. Where an acidic material is provided on a thermo-stable support, the thermo-stable support can include for example, one or more of silica, tin oxide, niobia, zirconia, titania, carbon, alpha-alumina, and the like. The oxides themselves (e.g., $ZrO_2$, $SnO_2$, $TiO_2$, etc.) which may optionally be doped with additional acid groups such as $SO_4$ may also be used as solid acid catalysts. Further examples of solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. The functional group is generally of the sulfonic acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer-copolymers which are solid acid catalysts. Nafion® is a registered trademark of E.I. du Pont de Nemours & Co.

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

"Support"=The catalysts described herein may be adhered to a support, such as silica, alumina, zirconia, titania, ceria, vanadia, carbon, heteropolyacids, silica-alumina, silica nitride, boron nitride, mixtures thereof, and the like. The foregoing list is illustrative, not exclusive. The active catalyst may be adhered to a nanoporous support, such as zeolites, nanoporous carbon, nanotubes, and fullerenes. The support itself may be surface-modified to modify surface moieties, especially surface hydrogen and hydroxyl moieties that may cause localized pH fluctuations. The support can be surface-modified by treating it with silanes, alkali compounds, alkali earth compounds, and the like. The surface chemistry of the support can also be modified by treatments that make it more acidic or basic, for example, by treating carbon supports with nitric acid or ammonia, respectively.

Overview:

In general, the conversion of glucose to HMF can follow two reaction pathways. One pathway is through a Lewis acid-catalyzed isomerization of glucose to fructose combined with the dehydration of fructose to HMF. See Scheme 1:

Scheme 1: Reaction scheme for the conversion of glucose to HMF catalyzed by the combination of a Lewis and a Brønsted acid.[1a, 4]

The other pathway is through the direct dehydration of glucose to HMF. See Scheme 2:

Scheme 2: Reaction scheme for Brønsted acid-catalyzed dehydration of glucose to HMF.[3]

HMF

Isomerization of Glucose to Fructose and Dehydration of Fructose to HMF:

From these two reaction pathways the one passing through fructose was hypothesized by the present inventors to be more selective towards HMF formation. It was thus further hypothesized by the present inventors that the combination of Lewis and Brønsted acidity could produce HMF by a combined isomerization/dehydration reaction of glucose to HMF, as illustrated in Scheme 3:

ber of conventional and well-known organic solvents, including non-polar organic solvents such as straight, branched, and cyclic alkanes (e.g., pentane, cyclopentane, hexane, cyclohexane, etc.) and aromatic organic solvents (e.g. benzene, toluene, and myriad other substituted benzene solvents). The organic extraction solution preferably comprises, consists essentially of; or consists of an alkylphenol (AP) as defined earlier. Preferred AP's for use in the method include:

Scheme 3: Conversion of glucose to HMF by a combined isomerization/dehydration reaction pathway.

Thus, described and claimed herein is a method of converting glucose to HMF in a biphasic reactor system in the presence of Lewis acid and Brønsted acid catalysts. As noted earlier, any Brønsted acid catalyst and Lewis acid catalyst may be used. The most preferred Lewis acid catalysts are $AlCl_3$, $SnCl_4$, $VCl_3$, $InCl_3$, $GaCl_3$, $LaCl_3$, $DyCl_3$ and $YbCl_3$. The most preferred Brønsted acid catalysts are mineral acids in general, HCl in particular.

The biphasic reactor includes an aqueous layer and a substantially water-immiscible organic extraction solution. The organic extraction solution may comprise any of a large num- -continued The most preferred AP for the organic layer is 2-sec-butylphenol (SBP).

Optionally, as noted above, the aqueous layer may contain dissolved NaCl in any amount up to the point where the aqueous layer is saturated with NaCl.

In the preferred version of the process, metal chlorides (Lewis acid catalysts) are dissolved in the aqueous layer, and the pH is lowered further by the addition of a Brønsted acid, such as HCl or other Brønsted acid (see definition above). (Depending on the strength of the acids used, addition of the Brønsted acid will not lower the pH beyond what it already was by the addition of the Lewis acid.) It is preferred that the pH of the aqueous phase be about 5 or less, about 4 or less, about 3.5 or less, about 3 or less, about 2.5 or less, about 2 or less, or about 1.8 or less. It is preferred that that the pH range of the aqueous phase be between about 1.5 and about 4; more preferably between about 1.8 and about 3.5, and more preferably still between about 1.8 and about 3. In the examples described herein, the pH was lowered to 2.5 by the addition of HCl, with the exception of $SnCl_4$ for which dissolution of the salt produced a solution with a pH of 1.8.

The rationale for using a biphasic reactor is that the reactive HMF product can be continuously extracted from the acidic aqueous phase, thereby minimizing condensation reactions of HMF with glucose that lead to solid humins and rehydration reactions of HMF to form levulinic and formic acid.[1a, 13] In this respect, alkylphenol compounds have been recently identified that are effective for the extraction of levulinic acid and furan compounds from acidic aqueous solutions.[14] As noted above, alkylphenols are the preferred extracting solvent for the removal of HMF from the reactive aqueous layer. Working examples demonstrating the conversion of glucose to HMF were performed at 443 K under autonomous pressure. The main products observed were fructose, HMF, and solid humins.

As shown in Table 1, entries 1-2, glucose can be converted in the presence of the mineral acid, HCl, without any metal chloride catalyst; however, the selectivity for production of HMF is only 30% at 91% conversion. While not being limited to any particular mechanism, it is thought that in the absence of an isomerization catalyst, the formation of HMF may follow a mechanism in which the open-chain form of glucose is dehydrated at the C-2 position, forming a carbocation which reacts with the hydroxyl group at C-5 position, forming tetrahydro-3,4-dihydroxy-5-(hydroxymethyl)-2-furaldehyde followed by further dehydration to form HMF (see Scheme 2 above). The addition of a Lewis acid salt clearly leads to a significant increase in HMF selectivity, as shown in Table 1, entries 3-10. The presence of $AlCl_3$ leads to 68% HMF selectivity at 91% conversion, with a short reaction time. Moderate HMF selectivities of 53, 52 and 50% were obtained at conversions of 92, 86 and 90% for the addition of $VCl_3$, $InCl_3$ and $GaCl_3$, respectively to the aqueous layer. $YbCl_3$, $DyCl_3$ and $LaCl_3$ were also studied, displaying HMF selectivities of 46, 41 and 44%, respectively. The addition of $SnCl_4$ to the aqueous layer led to a glucose conversion of 90% with 58% selectivity to HMF; however, the pH of this solution was 1.8. At this same pH of 1.8, $AlCl_3$ generated a conversion of 90% with 68% selectivity to HMF.

TABLE 1

Conversion of glucose to HMF in a biphasic system with SBP as extracting organic layer.[a]

| Entry | Catalyst | Conversion [%] | Selectivity [%] | Time [min] |
|---|---|---|---|---|
| 1 | — | 15 | 52 | 30 |
| 2 | — | 91 | 30 | 420 |
| 3 | $AlCl_3$ | 91 | 68 | 40 |
| 4 | $SnCl_4$ | 90 | 58 | 45 |
| 5 | $VCl_3$ | 92 | 53 | 90 |
| 6 | $GaCl_3$ | 90 | 50 | 120 |
| 7 | $InCl_3$ | 86 | 52 | 150 |
| 8 | $YbCl_3$ | 93 | 46 | 120 |
| 9 | $DyCl_3$ | 93 | 41 | 160 |
| 10 | $LaCl_3$ | 87 | 44 | 240 |

[a]Reaction conditions: 5 wt % glucose in water saturated with NaCl, reaction temperature of 443K, organic-to-aqueous mass ratio of 2, pH = 2.5 with the exception of entry 4 which has a pH = 1.8. Entries 3-5, glucose-to-Lewis acid molar ratio of 67. Entries 6-10, glucose-to-Lewis acid molar ratio of 13.

Although typical Lewis acids, such as metal halides, are generally considered to be inactive in water, Fringuelli, et al.[15] recently demonstrated that $AlCl_3$, $TiCl_4$ and $SnCl_4$ are active in Lewis acid-catalyzed reactions in water at pH<4. Metals salts can form different species depending on the pH of the aqueous solution. Aluminum, for example, can form the Keggin heteropolycation in alkaline aqueous solution, while it is present as solvated $Al^{+3}$ at pH<3.[16] For $SnCl_4$, the mononuclear species $Sn(OH)_y^{(4-y)+}$ has been proposed primarily in cationic form in pH<2.[16-17] At the pH employed in this study, vanadium is present as $VO_{2+}$, whereas all other metal ions are present as solvated cations.[16] Fringuelli, et al.,[15] have shown the pH of the solution plays a key role in controlling the Lewis acidity of metal halides in an aqueous solution. Therefore, in the system used in this work for glucose conversion to HMF, the acidic pH is believed to be responsible for the formation of the catalytically active metal species, thus facilitating glucose ring-opening and the subsequent dehydration reactions.

Figure 1A:
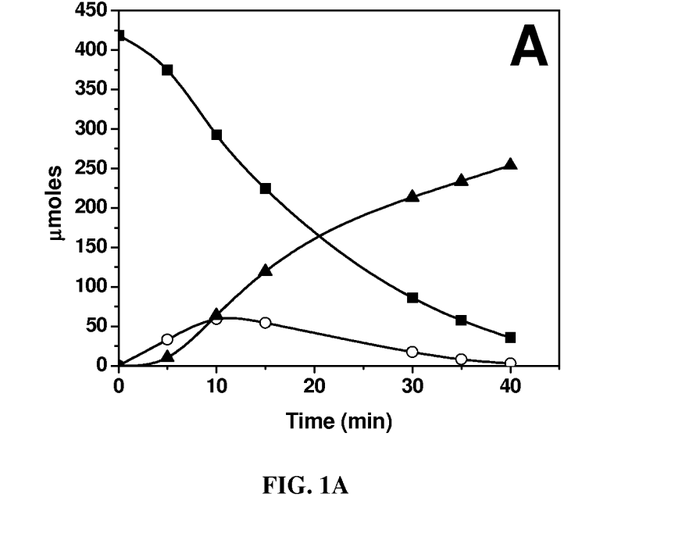
Figure 1B:
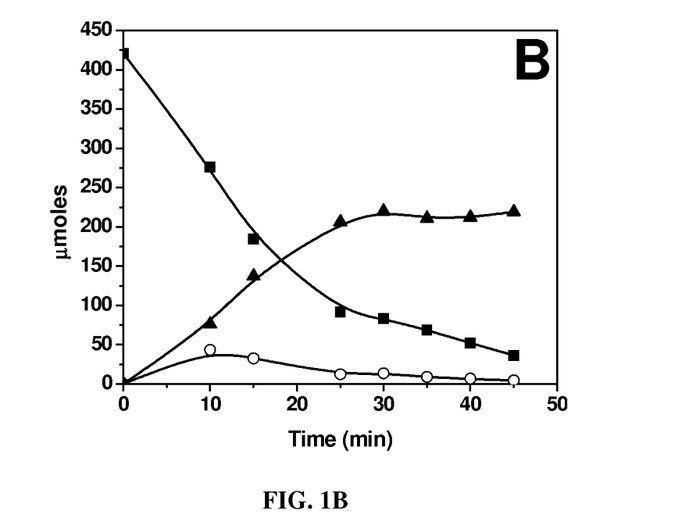
Figure 1C:
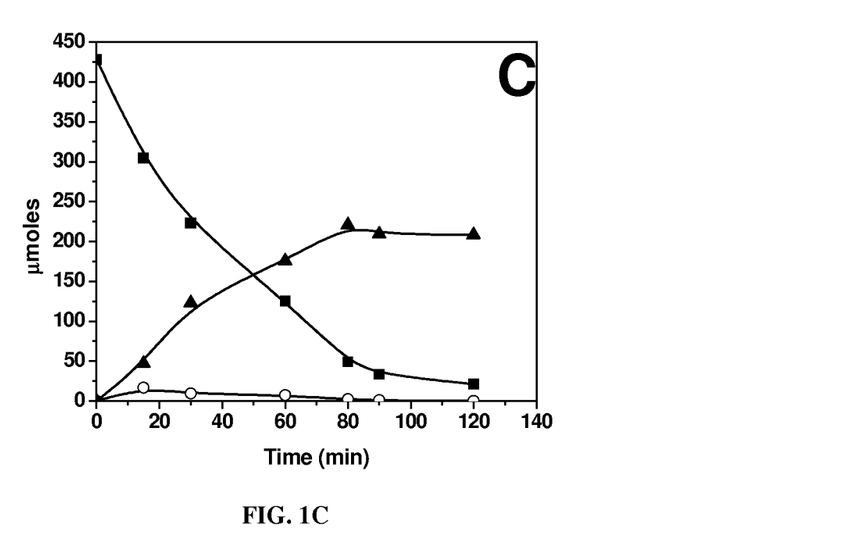
Figure 1D:
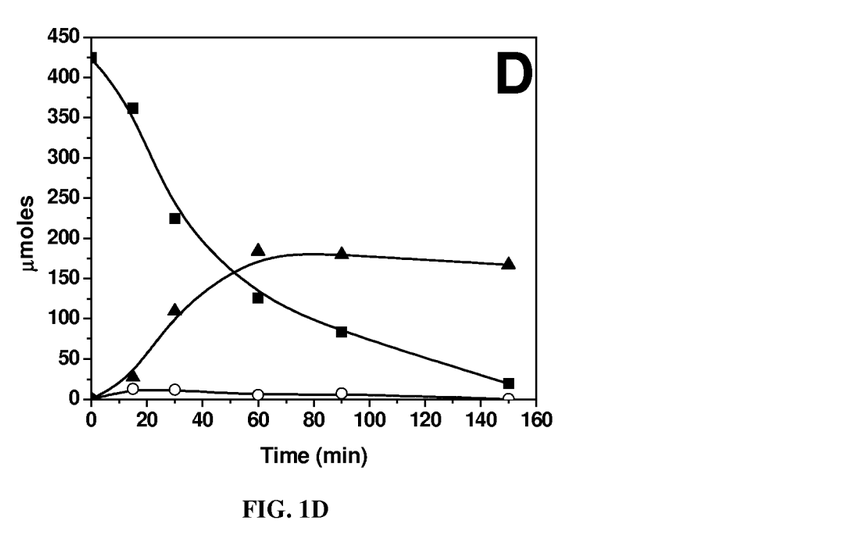
Figure 1E:
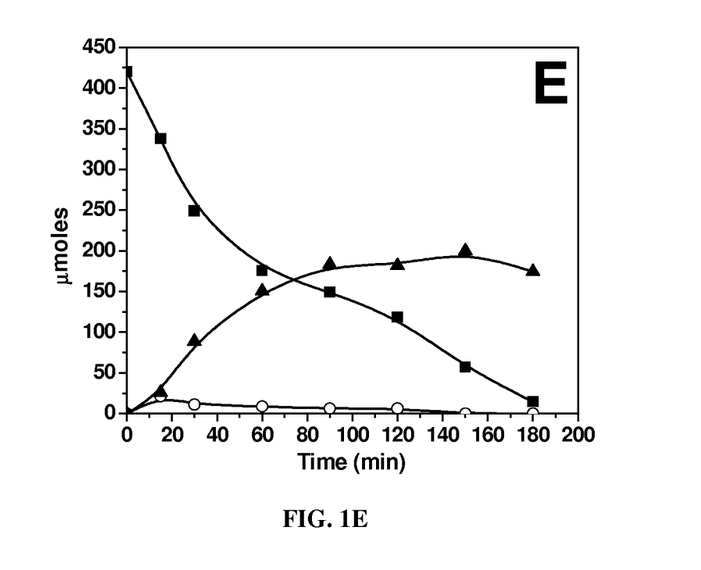
Figure 1F:
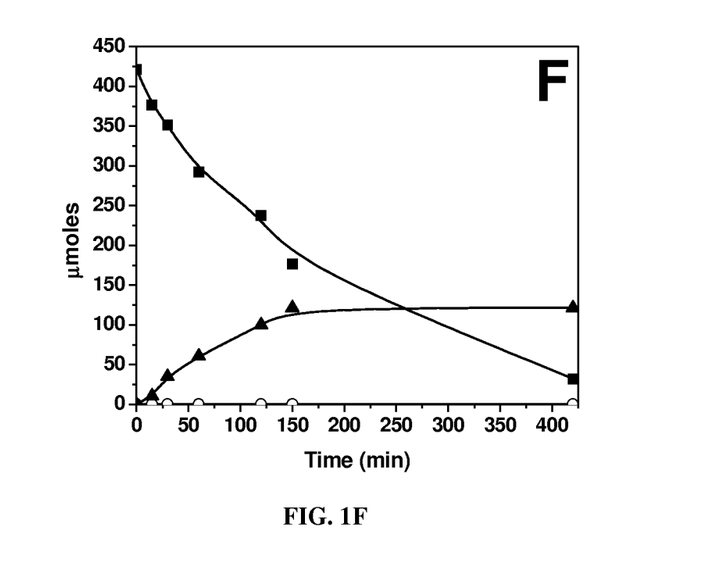
Figure 3:
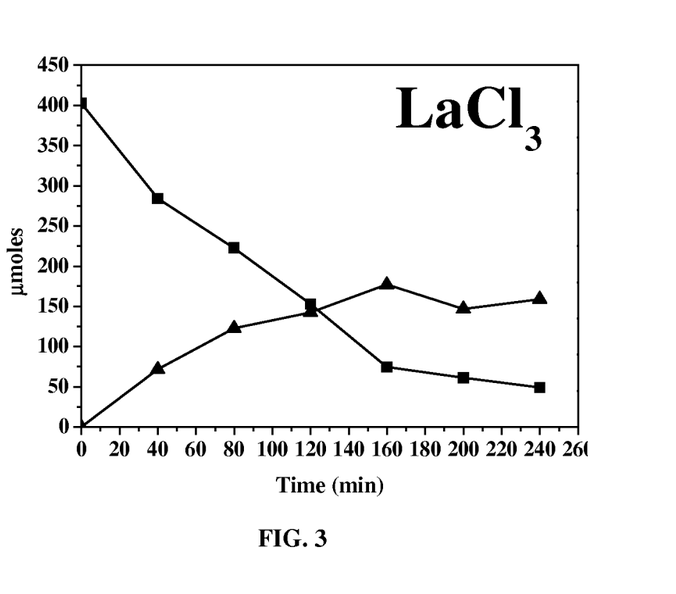
FIG. 3: Glucose conversion and HMF production versus time in a biphasic system with SBP in the presence of $LaCl_3$; (■)=glucose and (▲)=HMF.
Figure 4:
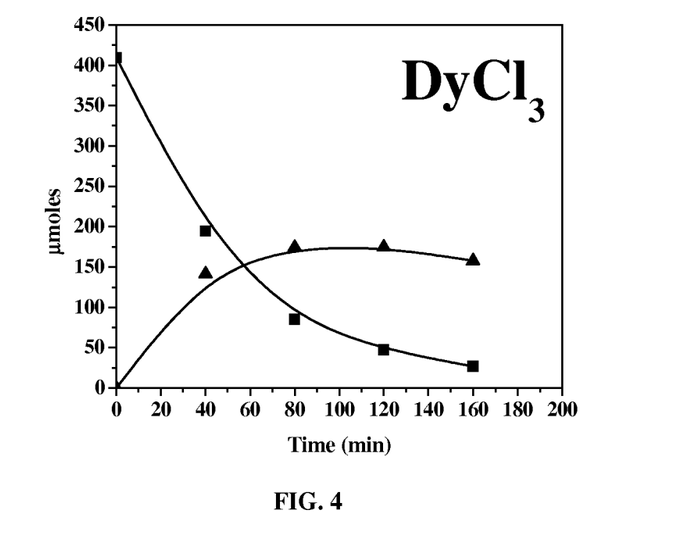
FIG. 4: Glucose conversion and HMF production versus time in a biphasic system with SBP in the presence of $DyCl_3$; (■)=glucose and (▲)=HMF.
Figure 5:
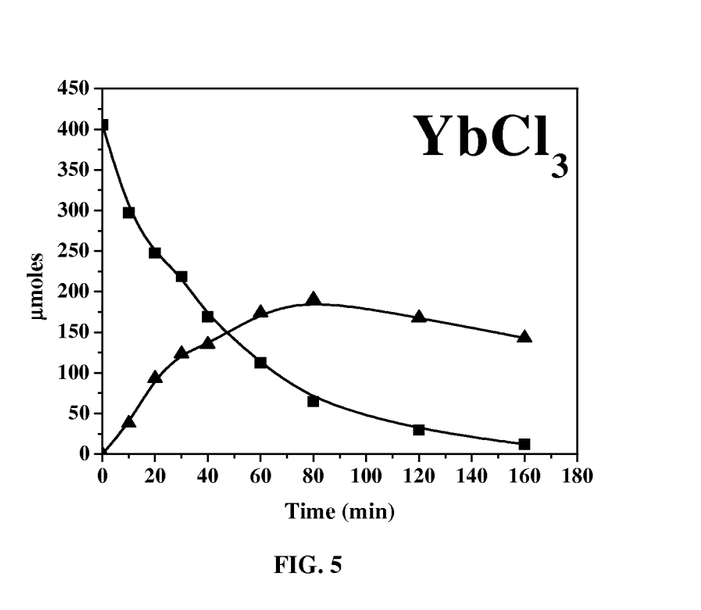
FIG. 5: Glucose conversion and HMF production versus time in a biphasic system with SBP in the presence of $YbCl_3$; (■)=glucose and (▲)=HMF.

FIGS. 1A, 1B, 1C, 1D, 1E, and 1F show the conversion of glucose to HMF as a function of time in the presence of $AlCl_3$, $SnCl_4$, $VCl_3$, $GaCl_3$, $InCl_3$ and without the metal chloride (respectively). FIGS. 3, 4, and 5 present reaction kinetics data for the lanthanide salts. In FIGS. 1A and 1B, fructose is observed to be a dominate intermediate which reaches a maximum concentration during the first 10 minutes of reaction in the presence of $AlCl_3$ and $SnCl_4$. At longer reaction times fructose is consumed with a concomitant formation of HMF. For reactions catalyzed by $VCl_3$, $GaCl_3$ and $InCl_3$, fructose is also produced as an intermediate (see FIGS. 1C, 1D, and 1E, respectively), but in lower quantities compared to $AlCl_3$ and $SnCl_4$. For the experiment performed in the absence of a Lewis acid salt (FIG. 1F), fructose is not observed, suggesting that HMF is produced from the acid catalyzed dehydration of glucose. It is clear from FIGS. 1A to 1F that reaction systems with higher fructose quantities show higher HMF yields, as observed for $AlCl_3$ and $SnCl_4$ (Table 1 entries 3-4). For systems with lower rates of fructose formation, such as for the cases of $VCl_3$, $GaCl_3$, and $InCl_3$, the direct dehydration of glucose to HMF could have a significant contribution, leading to lower selectivities to HMF.

The effectiveness of the Lewis acids studied in this work for the conversion of glucose to fructose can be understood in terms of their intrinsic properties, such as the Lewis acid softness and ionic radius. For example, aluminum is the hardest of the Lewis acids studied, and it should interact strongly with the oxygen atoms of the hydroxyl groups in glucose, which are hard Lewis bases. Similarly, the ionic radius of the Lewis acid metal cations can be related to the reactivity of glucose. For example, the activity for glucose conversion and HMF formation increases with decreasing ionic radii from $In^{+3} > Ga^{+3} > Al^{+3}$ and for the lanthanide series from $La^{+3} > Dy^{+3} > Yb^{+3}$. The increased catalytic activity with decreasing ionic radius can be attributed to stronger electrostatic interaction between glucose and the smaller cations, caused by an increase in the effective surface charge density of the ion.[18] Ionic radii in pm for the various metals are as follows $Al^{+3}=68$; $Ga^{+3}=76$; $In^{+3}=94$; $Yb^{+3}=101$; $Dy^{+3}=105$; and $La^{+3}=117$.

The dehydration of fructose to HMF with high yields has been reported in previous studies using mineral acids and salts in a biphasic reactor with organic solvents such as tetrahydrofuran (THF), methyl isobutyl ketone (MIBK), and 2-butanol.[13] In the present process, THF showed the highest partitioning of HMF into the organic phase. Therefore, the use of THF as the extracting organic layer was investigated. Results are shown in Table 2 for the production of HMF from glucose in a biphasic reactor using THF or SBP as the organic phase.

TABLE 2

Comparison between extracting organic layers for the conversion of glucose to HMF in a biphasic reaction system using $AlCl_3$ and HCl as catalysts.[a]

| Extracting Organic Layer | Conversion [%] | Selectivity [%] | % HMF in Org | % HCl in Org |
|---|---|---|---|---|
| THF | 80 | 71 | 93 | 30 |
| SBP | 88 | 70 | 97 | 0 |

[a]Reaction conditions: 5 wt % glucose in water saturated with NaCl, glucose-to-Lewis acid molar ratio of 67, pH = 2.5, reaction temperature of 443K, organic-to-aqueous mass ratio of 2.

Using SBP as the extracting solvent led to an HMF yield of 62%, and 97% of the HMF produced was extracted to the organic layer. In contrast, when using THF as the extracting solvent, an HMF yield of 57% was obtained, and 93% of the HMF was extracted into the organic phase. In addition to the higher HMF yields obtained using SBP, an important advantage of the SBP solvent with this biphasic system is that none of the HCl was detected in the organic layer, in contrast to the system with THF in which 30% of the HCl was extracted into the organic layer. The extraction of mineral acid into the organic solvent containing HMF can cause problems in further separation/purification steps, because of the high reactivity of HMF in the presence of acids. Nevertheless, using THF and other substantially immiscible organic solvents as the extracting solvent is within the scope of the process.

Figure 2:
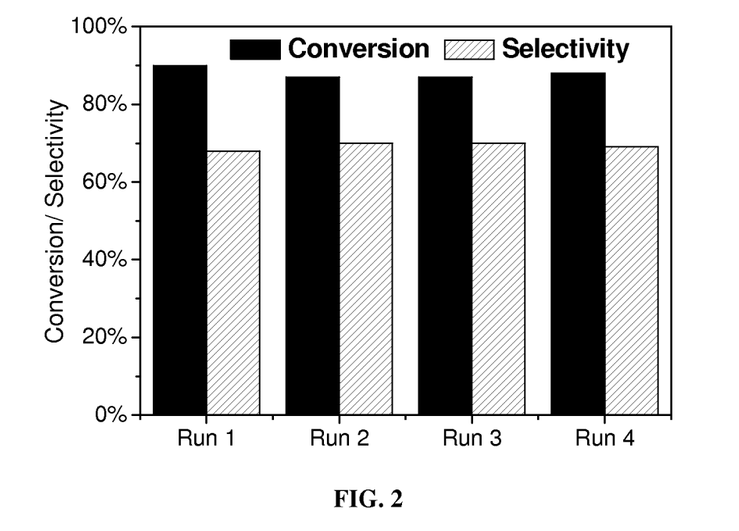
FIG. 2: Conversion and selectivity for production of HMF from glucose in consecutive runs using the same acidic aqueous solution containing $AlCl_3$ (Lewis acid) and HCl (Brønsted acid) as catalysts. Reaction conditions: 5 wt % glucose in water saturated with NaCl, reaction temperature of 443 K, organic-to-aqueous mass ratio of 2, pH=2.5, glucose-to-aluminum molar ratio of 67.

To further demonstrate the effectiveness of the water-SBP biphasic system with $AlCl_3$ and HCl as catalysts in the conversion of glucose to HMF, experiments were conducted to assess the extent to which the acidic aqueous layer could be recycled for glucose conversion. For these experiments, four consecutive runs were carried out, each with a reaction time of 40 min. Between each run, the organic layer containing HMF was extracted, and fresh SBP and glucose were added to the acidic aqueous solution in the reactor. For the first run, the conversion and selectivity were those observed in Table 1 Entry 3. For consecutive experiments, no significant decreases in conversion and selectivity were observed, as shown in FIG. 2.

Thus, the present disclosure shows that HMF can be produced efficiently from glucose in a biphasic reactor system using SBP as the organic extracting layer in contact with an aqueous phase saturated with NaCl, at pH equal to 2.5, and containing Lewis acidic metal halides, such as $AlCl_3$. The overall yield of HMF is 62% in this biphasic system using $AlCl_3$ and HCl as catalysts. The presence of the Lewis and Brønsted acids allows the conversion of glucose to proceed through a tandem reaction pathway involving isomerization of glucose to fructose followed by dehydration of the latter to HMF.

In the biphasic system employed here, the organic phase extracts 97% of the HMF from the aqueous phase, while the Lewis and Brønsted acid catalysts ($AlCl_3$ and HCl, respectively) remain in the aqueous phase. This reaction system has significant advantages over existing systems, such as recovering the HMF produced by removing the organic layer and recycling the reactive aqueous layer. Considering that all of the HMF in the organic phase can be recovered, a purified HMF yield of 60% can be obtained. Although this yield is lower than that achieved using ionic liquids[1b] and dimethylacetamide[1c] as solvents and $CrCl_2$ as catalyst, the present process avoids the use of expensive solvents and toxic salts. Furthermore, in these previous reaction systems, the yield of HMF is based on the reaction mixture, and further separation and purification of HMF from the reactive solution are required, leading to additional costs and product loss.

EXAMPLES

The following examples are included solely to provide a more complete disclosure of the method described and claimed herein. The examples do not limit the scope of the claims in any fashion.

Experimental Section

Biphasic dehydration reactions were carried out in 10 ml thick-walled glass reactors (Alltech, Deerfield, Ill.) heated in an oil bath at 443 K. The oil temperature and magnetic stirring were controlled by an Isotemp digital stirring hotplate (Fisher Scientific, a wholly owned subsidiary of ThermoFisher Scientific, Waltham, Mass.). Preparation of the aqueous layer consisted of using solutions containing 5 mM $AlCl_3$, $SnCl_4$ or $VCl_3$ and adjusting their pH to 2.5 with HCl, with the exception of the 5 mM $SnCl_4$, because a $SnCl_4$ solution at this concentration has a pH of 1.8. Solutions with 25 mM $InCl_3$, $GaCl_3$, $LaCl_3$, $DyCl_3$, or $YbCl_3$ were prepared and adjusted to a pH of 2.5. The pH-adjusted solutions were saturated with NaCl, and glucose was added to obtain a 5 wt % aqueous glucose feed. In a typical experiment, 1.5 g of the aqueous feed and 3.0 g of 2-sec-butylphenol (SBP) (Aldrich, St. Louis, Mo.) were added to the reactor. The reactor was placed in the oil bath at 443 K and stirred at 1200 rpm. Reactors were removed from the oil bath at specific reaction times and cooled in a dry ice/ethylene glycol slurry. For recycle experiments, an aqueous solution with 5 mM $AlCl_3$ was first prepared and adjusted to a pH of 2.5 with HCl. This mixture was saturated with NaCl, glucose was added to reach 5 wt %, and 1.5 g of the aqueous feed was added to a 10 ml thick-walled glass reactor containing 3.0 g of SBP. The reactor was heated in an oil bath to 443 K with stirring at 1200 rpm for 40 min. Upon completion of the reaction, reactors were cooled in a dry ice/ethylene glycol slurry. The organic layer was extracted and glucose added to the remaining aqueous layer to obtain a 5 wt % glucose mixture. Fresh SBP was added to the reactor, and the reaction was carried out for consecutive runs, as described previously.

Experiments performed to compare SBP with THF as the extracting organic layer were performed in a 50 ml pressure vessel (Hastelloy C-276, Parr Instrument, Moline, Ill.). In a typical experiment, 8 g of the aqueous solution consisting of 5 wt % glucose and $AlCl_3$ (with a glucose-to-aluminum ratio of 67, adjusted to a pH of 2.5 and saturated with NaCl) were added to the vessel, followed by addition of 16 g of the organic layer. When THF was used as the extracting organic layer, the solvent was saturated with a NaCl-water mixture prior to contact with the aqueous feed mixture. The pressure vessel was sealed, stirred with a magnetic stir bar, and heated with an external heating mantle to 443 K. The reactor was cooled in an ice bath upon completion of the reaction.

For all biphasic experiments, the organic and aqueous phases were separated and analyzed for quantification of glucose, fructose, and HMF by HPLC analysis. HPLC analysis was carried out using a Waters e2695 HPLC system equipped with a 2998 PDA UV detector (320 nm) and a 2414 refractive index detector maintained at 333 K (Waters Corp., Milford, Mass.). Aqueous layers were analyzed using an Aminex HPX-87H column (Biorad, Hercules, Calif.) at 353 K, using 0.005 M $H_2SO_4$ as the mobile phase at a flow rate of 0.6 ml $min^{-1}$. Organic layers were analyzed using a Waters 2695 HPLC system equipped with a 996 PDA UV detector and a Zorbax SB-C18 reverse phase column (Agilent, Santa Clara, Calif.) at 308 K, using an acetonitrile:water gradient at a flow rate of 1 ml $min^{-1}$. Glucose and fructose were monitored using the refractive index detector, and HMF production was monitored using UV detectors (320 nm). Conversions are defined as the moles of glucose reacted divided by the moles of glucose fed. Selectivity to HMF was calculated as the moles of HMF produced divided by the moles of glucose reacted.

REFERENCES CITED (1) (a) Román-Leshkov, Y.; Chheda, J. N.; Dumesic, J. A., *Science* 2006, 312, 1933-1937; (b) Zhao, H.; Holladay, J. E.; Brown, H.; Zhang, Z. C., *Science* 2007, 316, 1597-1600; (c) Binder, J. B.; Raines, R. T., *J. Am. Chem. Soc.* 2009, 131, 1979-1985; (d) Corma, A.; Iborra, S.; Velty, A., *Chem. Rev.* 2007, 107, 2411-2502; (e) Zakrzewska, M. E.; Bogel-Łukasik, E.; Bogel-Łukasik, R., *Chem. Rev.* 2010, 111, 397-417.

(2) (a) Gandini, A., Belgacem, M. N., *Prog. Polymer Science* 1997, 22, 1203-1379; (b) Moreau, C., Belgacem, M. N., Gandini, A., *Top. Catal.* 2004, 27, 11-29; (c) Buntara, T.; Noel, S.; Phua, P. H.; Melián-Cabrera, I.; de Vries, J. G.; Heeres, H. J., *Angew. Chem. Int. Ed.* 2011, 50, 7083-7087; (d) Lewkowski, J., *Arkivoc* 2001, 17-54.

(3) Robyt, J. F., *Essentials of Carbohydrate Chemistry*; Springer: New York 1998; p 48-74.

(4) Román-Leshkov, Y.; Moliner, M.; Labinger, J. A.; Davis, M. E., *Angew. Chem. Int. Ed.* 2010, 49, 8954-8957.

(5) Nagorski, R. W.; Richard, J. P., *J. Am. Chem. Soc.* 2001, 123, 794-802.

(6) Yang, B. Y.; Montgomery, R., *Carbohyd. Res.* 1996, 280, 27-45.

(7) Pidko, E. A.; Degirmenci, V.; van Santen, R. A.; Hensen, E. J. M., *Angew. Chem. Int. Ed.* 2010, 49, 2530-2534.

(8) (a) Hu, S. Q.; Zhang, Z. F.; Song, J. L.; Zhou, Y. X.; Han, B. X., *Green Chem* 2009, 11, 1746-1749; (b) Fristrup, P.; Stahlberg, T.; Rodriguez-Rodriguez, S.; Riisager, A., *Chem-Eur. J.* 2011, 17, 1456-1464; (c) Chidambaram, M.; Bell, A. T., *Green Chem.* 2010, 12, 1253-1262.

(9) Moreau, C.; Finiels, A.; Vanoye, L., *J. Mol. Catal. A: Chem.* 2006, 253, 165.

(10) Huang, R.; Qi, W.; Su, R.; He, Z., *Chem. Comm.* 2010, 46, 1115-1117.

(11) Takagaki, A.; Ohara, M.; Nishimura, S.; Ebitani, K., *Chem. Comm.* 2009, 6276-6278.

(12) Nikolla. E.; Román-Leshkov, Y.; Moliner, M.; Davis, M. E., *ACS Catal.* 2011, 1, 408-410.

(13) Román-Leshkov, Y.; Dumesic, J. A., *Top. Catal.* 2009, 52, 297-303.

(14) Alonso, D. M.; Wettstein, S. G.; Bond, J. Q.; Root, T. W.; Dumesic, J. A., *Chem Sus Chem* 2011, 4, 1078-1081.

(15) (a) Fringuelli, F.; Pizzo, F.; Vaccaro, L., *Tetrahedron Lett.* 2001, 42, 1131-1133; (b) Fringuelli, F.; Pizzo, F.; Vaccaro, L., *J. Org. Chem.* 2001, 66, 4719-4722.

(16) Baes, C. F.; Mesmer, R. E., *The Hydrolysis of Cations*; Wiley: New York, 1976.

(17) Jackson, K. J.; Helgeson, H. C., *Geochim. Cosmochim. Ac.* 1985, 49, 1-22.

(18) (a) Ishida, H.; Seri, K., *J. Mol. Catal. A: Chem.* 1996, 112, 163-165; (b) Seri, K.; Inoue, Y.; Ishida, H., *Bull. Chem. Soc. Jpn.* 2001, 74, 1145-1150.

What is claimed is:

1. A process to make hydroxymethylfurfural (HMF) from glucose, glucose-containing oligomers, glucose-containing polymers, or combinations thereof, the process comprising:
   reacting a feedstock solution comprising glucose, glucose-containing oligomers, glucose-containing polymers, or combinations thereof, in the presence of a homogeneous Brønsted acid catalyst and a homogeneous Lewis acid catalyst, in an aqueous reaction solution, to yield a product solution comprising HMF; and
   extracting the HMF into a substantially immiscible organic extraction solution, wherein the substantially immiscible organic extraction solution comprises at least one alkylphenol.

2. The process of claim 1, wherein the at least one alkylphenol is selected from the group consisting of:

wherein $R^1$-$R^5$ are independently selected from the group consisting of hydrogen, hydroxyl, esters, ethers, carboxylic acids, and $C_1$-$C_{24}$ linear, branched, or cyclic alkyl or alkene, provided that at least one of $R^1$-$R^5$ is an alkyl group.

3. The process of claim 2, wherein $R^1$-$R^5$ are independently selected from the group consisting of hydrogen, hydroxyl, esters, ethers, carboxylic acids, and $C_1$-$C_{12}$ linear, branched, or cyclic alkyl, provided that at least one and no more than two of $R^1$-$R^5$ is an alkyl group.

4. The process of claim 2, wherein $R^1$-$R^5$ are independently selected from the group consisting of hydrogen, hydroxyl, esters, ethers, carboxylic acids, and $C_1$-$C_6$ linear, branched, or cyclic alkyl, provided that at least one and no more than two of $R^1$-$R^5$ is an alkyl group.

5. The process of claim 1, wherein the Lewis acid catalyst is selected from the group consisting of Lewis acids comprising a lanthanoid metal, a metal from any of Groups 4, 5, 13, 14 and 15 of the periodic table of the elements, and combinations thereof; and the Brønsted acid catalyst is selected from the group consisting of mineral acids, organic acids, and heteropolyacids, and combinations thereof.

6. The process of claim 1, wherein the aqueous reaction solution further comprises NaCl dissolved therein.

7. The process of claim 6, wherein the aqueous reaction solution is saturated with NaCl.

8. A process to make hydroxymethylfurfural (HMF) from glucose, glucose-containing oligomers, glucose-containing polymers, or combinations thereof, the process comprising:

reacting a feedstock solution comprising glucose, glucose-containing oligomers, glucose-containing polymers, or combinations thereof, in the presence of a homogeneous Brønsted acid catalyst and a homogeneous Lewis acid catalyst, in a reaction vessel containing a biphasic reaction medium comprising an aqueous reaction solution and a substantially immiscible organic extraction solution comprising at least one alkylphenol, to yield an amount of HMF in the aqueous reaction solution, and wherein at least a portion of the HMF formed in the aqueous reaction solution is extracted into the organic extraction solution.

9. The process of claim 8, wherein the at least one alkylphenol is selected from the group consisting of:

wherein $R^1$-$R^5$ are independently selected from the group consisting of hydrogen, hydroxyl, esters, ethers, carboxylic acids, and $C_1$-$C_{24}$ linear, branched, or cyclic alkyl or alkene, provided that at least one of $R^1$-$R^5$ is an alkyl group.

10. The process of claim 9, wherein $R^1$-$R^5$ are independently selected from the group consisting of hydrogen, hydroxyl, esters, ethers, carboxylic acids, and $C_1$-$C_{12}$ linear, branched, or cyclic alkyl, provided that at least one and no more than two of $R^1$-$R^5$ is an alkyl group.

11. The process of claim 9, wherein $R^1$-$R^5$ are independently selected from the group consisting of hydrogen, hydroxyl, esters, ethers, carboxylic acids, and $C_1$-$C_6$ linear, branched, or cyclic alkyl, provided that at least one and no more than two of $R^1$-$R^5$ is an alkyl group.

12. The process of claim 8, wherein the Lewis acid catalyst is selected from the group consisting of Lewis acids comprising a lanthanoid metal, a metal from any of Groups 4, 5, 13, 14 and 15 of the periodic table of the elements, and combinations thereof; and the Brønsted acid catalyst is selected from the group consisting of mineral acids, organic acids, heteropolyacids, and combinations thereof.

13. The process of claim 8, wherein the aqueous reaction solution further comprises NaCl dissolved therein.

14. The process of claim 8, wherein the aqueous reaction solution is saturated with NaCl.

\* \* \* \* \*

UNITED STATES PATENT AND TRADEMARK OFFICE
CERTIFICATE OF CORRECTION

| | | |
|---|---|---|
| PATENT NO. | : 8,642,791 B2 | Page 1 of 1 |
| APPLICATION NO. | : 13/313389 | |
| DATED | : February 4, 2014 | |
| INVENTOR(S) | : James A. Dumesic et al. | |

It is certified that error appears in the above-identified patent and that said Letters Patent is hereby corrected as shown below:

Title Page, Item (54) and in the Specification, at column 1, line 2, in the title, please insert the word -- OF -- after the word PRODUCTION.

Signed and Sealed this
Twenty-ninth Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO.         : 8,642,791 B2
APPLICATION NO.    : 13/313389
DATED              : February 4, 2014
INVENTOR(S)        : James A. Dumesic et al.

Page 1 of 1

It is certified that error appears in the above-identified patent and that said Letters Patent is hereby corrected as shown below:

Title Page, Item (73), after Wisconsin Alumni Research Foundation, Madison, WI (US) please insert --Iowa State University Research Foundation, Inc., Ames, IA (US)--

Signed and Sealed this
Fifth Day of July, 2016

Michelle K. Lee
*Director of the United States Patent and Trademark Office*